United States Patent [19]
Johnston

[11] Patent Number: 4,939,927
[45] Date of Patent: Jul. 10, 1990

[54] DEVICE TO MEASURE THE TENDERNESS OF MEAT

[76] Inventor: Geoffrey Johnston, "Claremont", Bega, New South Wales, Australia, 2550

[21] Appl. No.: 236,523
[22] PCT Filed: Aug. 31, 1987
[86] PCT No.: PCT/AU87/00298
  § 371 Date: Jun. 6, 1988
  § 102(e) Date: Jun. 6, 1988
[87] PCT Pub. No.: WO88/01742
  PCT Pub. Date: Mar. 10, 1988

[30] Foreign Application Priority Data
  Sep. 3, 1986 [AU] Australia .............. PH7822

[51] Int. Cl.⁵ .............................................. G01N 3/42
[52] U.S. Cl. ........................................ 73/81; 426/231
[58] Field of Search ................... 73/81, 83; 426/231

[56] References Cited

U.S. PATENT DOCUMENTS

| | | | |
|---|---|---|---|
| 2,446,956 | 8/1948 | Ross | 73/81 |
| 3,078,710 | 2/1963 | Palmer | 426/231 X |
| 3,182,491 | 5/1965 | Tschirf et al. | 73/83 |
| 3,201,976 | 8/1965 | Starrett et al. | 73/81 |
| 3,264,866 | 8/1966 | Bouschart et al. | 73/78 |
| 3,498,120 | 3/1970 | MacMillan | 73/81 X |
| 3,554,018 | 1/1971 | Anderson et al. | 73/81 |
| 3,732,727 | 5/1973 | Hinnergardt et al. | 73/81 |
| 4,019,376 | 4/1977 | Iwasahi | 73/81 |

FOREIGN PATENT DOCUMENTS

| | | |
|---|---|---|
| 444890 | 8/1970 | Australia . |
| 524041 | 8/1982 | Australia . |
| 820815 | 11/1951 | Fed. Rep. of Germany .......... 73/81 |
| 1157451 | 5/1985 | U.S.S.R. . |

OTHER PUBLICATIONS

"Objective and Subjective Measurements for Meat Tenderness"; *Proceedings Meat Tenderness Symposium* 1963; pp. 135, 142–155; A. M. Pearson.
"Methods of Meat Texture Measurement Viewed from the Background of Factors Affecting Tenderness". *Advances in Food Research*, vol. 14, 1965; pp. 33,74,75, and 78–85; Alina Surmacka Szczesnick et al.
Derwent Abstract Accession No. 85-315287/50, Class S03, SU,A, 1157451 (Moscow Meat Dairy Inst.) May 23, 1985 (23.05.85).

*Primary Examiner*—Tom Noland
*Attorney, Agent, or Firm*—Ladas & Parry

[57] ABSTRACT

A meat probe for determining the tenderness of meat. A piston (12) slidably mounted in a body (13) has a probe member (11) attached thereto. Force is applied to the piston by a spring (16) and a second piston (15) is advanced by a trigger assembly (18). Scales associated with the first and second pistons measure both the depth of penetration of the probe and the force required for penetration. The measurements may be used alone, or in conjunction, in determining tenderness.

9 Claims, 2 Drawing Sheets

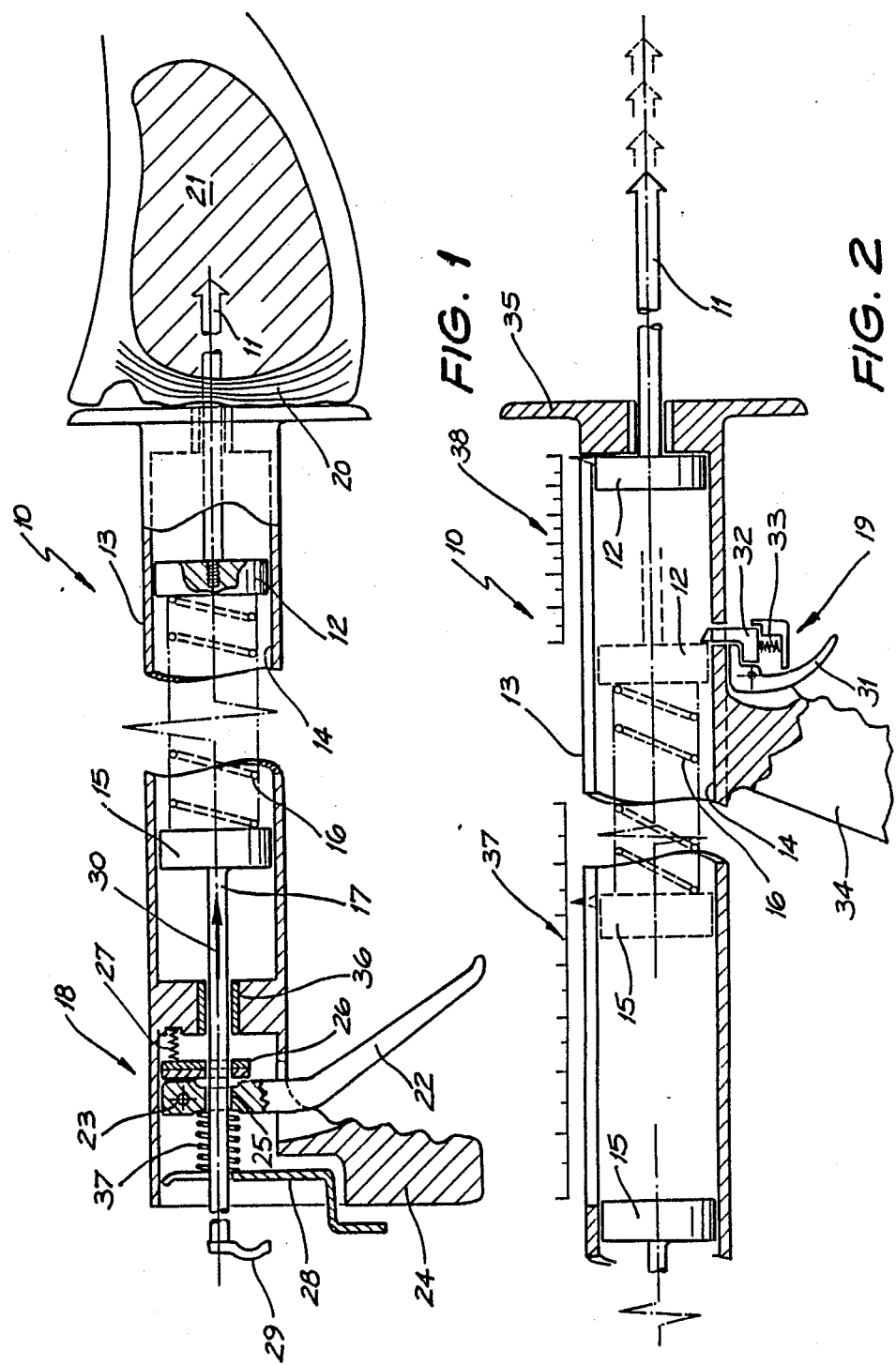

DEVICE TO MEASURE THE TENDERNESS OF MEAT

BACKGROUND OF THE INVENTION

The present invention relates to the meat industry and more particularly to a probe to aid in classifying meat in respect of tenderness.

Traditionally, meat, including beef, lamp and port, has generally been classified by means of inspection carried out preferably by a trained inspector. However, it is a disadvantage of this method that the classification is generally unreliable due to varying standards between inspectors, and that inspection is generally just a visual inspection.

Various devices have also been proposed to aid in detecting the tenderness of meat. These devices have generally been unsuccessful.

SUMMARY OF THE INVENTION

It is the object of the present invention to overcome or substantially ameliorate the above disadvantages.

There is disclosed herein a meat probe to aid in determining the tenderness of meat, said probe comprising a body having a forward end to engage a meat sample, an elongated probe member movably mounted on the body so as to be movable forward from said end relative thereto along the longitudinal axis of the member, force applying means to apply a force to said member to cause said member to penetrate the meat sample force adjustment means to control said force applying means so that the force applied to said member increases until said probe penetrates said sample, and indicator means to provide an indication of the magnitude of the force applied to said member.

There is further disclosed herein a meat probe to aid in determining the tenderness of meat, said probe comprising a body having a forward end to engage a meat sample, an elongated probe member movably mounted on said body so as to be movable relative thereto forward from said end along the longitudinal axis of said member, from a retracted position to an extended position, force applying means to apply a force to said member to cause said member to penetrate said meat sample by moving said member from said retracted position to said extended position, retaining means to retain said member in said retracted position, which retaining means is operable to release said member to enable said member to move to the extended position thereof, an indicator means to provide an indication of the depth of penetration of said probe member.

BRIEF DESCRIPTION OF THE DRAWING

A preferred form of the present invention will now be described by way of example with reference to the accompanying drawings, wherein:

FIG. 1 is a schematic sectioned plan view of a device to aid in determining the tenderness of a meat sample;

FIG. 2 is a schematic sectioned side elevation of the device of FIG. 1; and

DESCRIPTION OF THE PREFERRED EMBODIMENT

Figure 3:
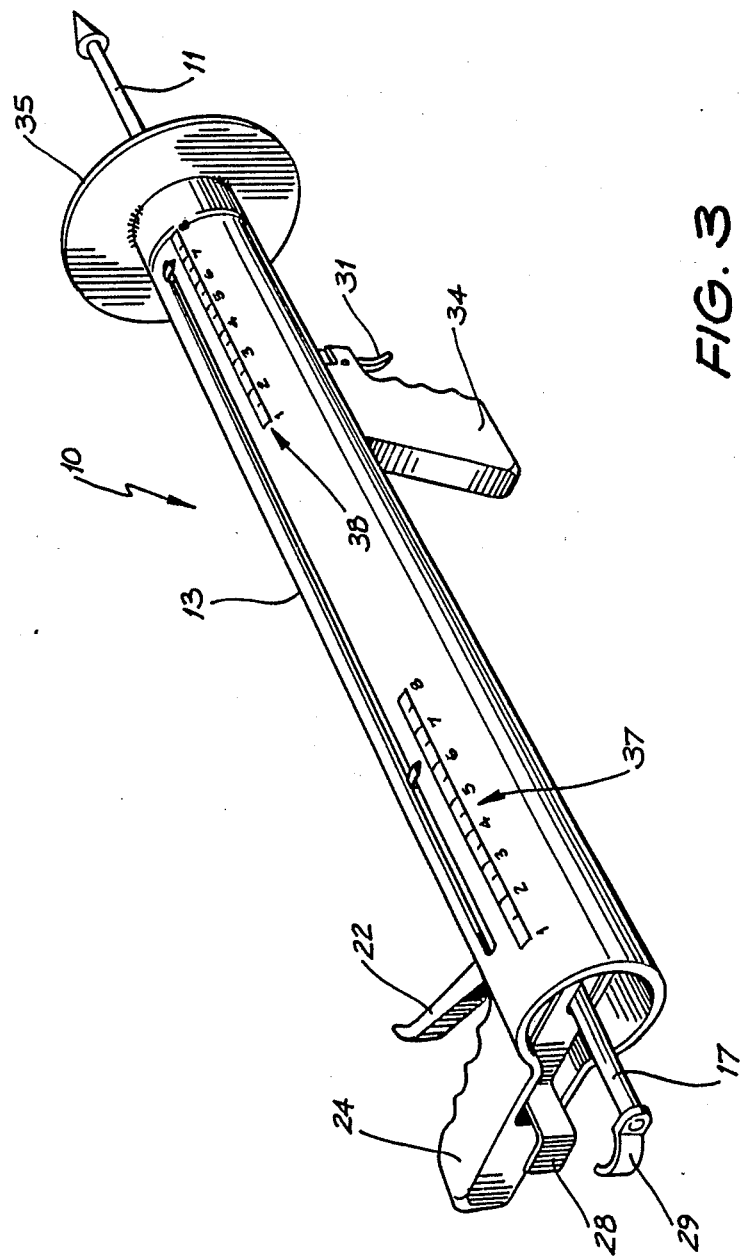
FIG. 3 is a schematic perspective view of the device of FIGS. 1 and 2.

In the accompanying drawings there is schematically depicted a device 10 to aid in the classification of mean (in the form of whole carcasses) in respect of eating quality. That is, to rank carcasses in order of their toughness.

The device 10 of the accompanying drawings performs two tests. The first of these tests determines the force required to have the probe member 11 penetrate the connective tissue 20 extending between a pair of ribs of a carcass. Preferably the connective tissue tested would be the connective tissue extending between the twelfth and thirteenth ribs. The second test requires the measurement of the distance the probe 11 penetrates the eye 21 behind the connective tissue 20.

The device 10 includes a body 13, of generally cylindrical configuration, having an internal cylindrical surface 14. Slidably mounted within the body 13 is a pair of pistons 12 and 15 between which there extends a spring 16. Fixed to the piston 12 is the meat probe 11. Extending rearwardly from the piston 15 is a piston rod 17 operatively moved by the trigger assembly 18. The trigger assembly 18 basically performs the above discussed first test. There is further provided a trigger assembly 19 which controls the second test.

The trigger assembly 18 includes a trigger 22 which is pivotally mounted at its upper end to the body 13 by means of a pin 23. Behind the trigger 22 is a handle 24 which enables the operator to squeeze the trigger 22 towards the handle 24. The trigger 22 is provided with a passage 25 through which the piston rod 17 passes. Located adjacent the upper end of the trigger 22 are co-operating plates 26 which selectively engage the piston rod 17. The plates 26 are biassed into engagement with the trigger 22 by means of a spring 27. Pivotally mounted adjacent the rear of the body 13 is a release member 28 which also engages the rod 17. More particularly the release member 28, at its upper end, is of a forked configuration so that the rod 17 passes through the release member 28. The extremity of the piston rod 17 is provided with a finger grip member 29 enabling an operator to grip the rod 17 to cause movement of the rod 17 to the rest position.

The trigger assembly 18 causes stepwise movement of the piston rod 17 in the direction of the arrow 30. By the operator causing pivoting of the trigger 22, the plates 26 are tilted and frictionally engage the rod 30. Further movement of the trigger 22 then causes movement of the rod 17 in the direction of the arrow 30. Upon the trigger 22 being released, the rod 17 is retained in position by the release member 28 frictionally engaging the rod 17. Each actuation of the trigger 22 causes incremental advancement of the rod 17.

The trigger assembly 19 includes a pivotally mounted trigger 31 which actuates a catch 32. The catch 32 projects into the body 13 so as to engage the piston 12. More particularly the catch 32 prevents movement of the piston 12 beyond a predetermined position. The catch member 32 is movable and is biased to a position projecting into the body 13 by means of a spring 33. The trigger 31 upon pivoting, causes the catch 32 to be moved to a position allowing movement of the piston 12 beyond the abovementioned predetermined position. A handle 34 is also provided for ease of operation of the trigger 31.

The forward end of the body 13 is provided with a plate 35 which abuts the carcass and through which probe member 11 projects. A guide bush 36 is also provided to guide the piston rod 17.

The body 13 is provided with two sets of calibration markings 37 and 38. The calibration markings 37 would indicate the force required to cause the probe 11 to puncture the connective tissue 20, while the calibration markings 38 would indicate the degree of penetration into the eye 21.

In operation of the above described device 10, the operator would first grip the rod 17 and withdraw the rod 17 until the piston 15 abutted the guide 36. Additionally the probe 11 would be gripped and moved into the body 13 until the piston 12 was retained in position by the catch 32. The plate 35 would be placed against the carcass and the trigger 22 manipulated to cause incremental advancement of the rod 17. This movement of the rod 17 would cause movement of the piston 15 and subsequent compression of the spring 16 between the pistons 12 and 15. Initially insufficient force would be applied to the probe 11 to enable the probe 11 to puncture the connective tissue 20. However upon the rod 17 being moved a sufficient distance, sufficient force would be applied to the piston 12 to cause the probe 11 to puncture the connective tissue 20. Upon this occuring, the probe 11 will then penetrate into the eye 21. However this movement of the probe 11 would be halted by engagement of the piston 12 with the catch 32. The trigger 31 would then be manipulated releasing the piston 12 and enabling the probe 11 to penetrate until there was insufficient force applied to the piston 12 by the spring 13 to overcome any further resistance.

The above described method of operation would give two readings. The first reading on the calibration 37 would provide the force required to cause puncturing of the connective tissue 20. The second reading on the calibration 38 would provide a measurement of the degree of penetration of the probe 11.

In operation of the trigger mechanism 18, it should be appreciated that rearward movement of the rod 17 under the influence of the spring 16 would be prohibited by the release member 28 being tilted by the spring 37. This tilting of the release member 28 causes the release member 28 to frictionally engage the rod 17. However an operator can release the rod 17 by depressing the release member 28 towards the handle 24.

For comparative reasons, it may be desirable to move the piston 15 in between the two operations so that a predetermined force is applied to the piston 12 prior to actuation of the trigger 31.

It should further be appreciated that a range of probes 11 may be provided. This range may include variations in length and tip configurations. Such a variety of probes 11 would enable the device 10 to be used with different qualities and types of meat.

I claim:

1. A meat probe to aid in determining the tenderness of meat, said probe comprising:
    a generally cylindrical body having a forward end having formed therein an aperture through which projects an elongated probe member, the probe member having a first piston directly affixed thereto, the first piston reciprocable within the body;
    a second piston reciprocable within the body, the second piston having attached thereto a piston rod, the rod extending beyond a rear end of the cylindrical body opposite the forward end;
    a resilient means interposed between the first and second pistons within the body;
    the rear end of the body housing a means for advancing the piston rod and a means for releasing the piston rod;
    the body having exterior calibrated markings which cooperate with a portion of the second piston to indicate the advancement of the second piston within the body.

2. The meat probe of claim 1, wherein:
    the means for advancing the piston rod comprises a trigger hingedly attached to the interior of the body, the trigger having a passage therethrough, the piston rod passing through the passage, and co-operating plates which are biased into engagement with the trigger, the plates selectively engaging and advancing the piston rod in an incremental fashion when the trigger is activated.

3. The meat probe of claim 1, wherein:
    the body further comprises a longitudinal slot, the exterior calibrated markings provided adjacent and along the slot, wherein a portion of the second piston is visible through the slot.

4. A meat probe to aid in determining the tenderness of meat, said probe comprising:
    a generally cylindrical body having a forward end having formed therein an aperture through which projects an elongated probe member, the probe member having a first piston directly affixed thereto, the first piston reciprocable within the body;
    a second piston reciprocable within the body, the second piston having attached thereto a piston rod, the rod extending beyond a rear end of the cylindrical body opposite the forward end;
    a resilient means interposed between the first and second pistons within the body;
    the rear end of the body housing a means for advancing the piston rod and a means for releasing the piston rod;
    a catch located between the forward and rear ends of the body, the catch activted from a first position in which it restrains the first piston to a second position in which it is disengaged from the first piston allowing the first piston to advance, the catch activated by a trigger on the exterior of the body;
    the body further comprising a calibrated means for indicating the advancement of first piston after activation of the trigger.

5. The meat probe of claim 4, wherein:
    the means for indicating the advancement of the first piston comprises a longitudinal slot formed in the body, the slot having calibrated markings adjacent thereto, a portion of the first piston visible through the slot.

6. A meat probe to aid in determining the tenderness of meat, said probe comprising:
    a generally cylindrical body having a forward end having formed therein an aperture through which projects an elongated probe member, the probe member having a first piston directly affixed thereto, the first piston reciprocable within the body;
    a second piston reciprocable within the body, the second piston having attached thereto a piston rod, the rod extending beyond a rear end of the cylindrical body opposite the forward end;
    a resilient means interposed between the first and second pistons within the body;
    the rear end of the body housing a means for advancing the piston rod and a means for releasing the piston rod;

a catch located between the forward and rear ends of the body, the catch activated from a first position in which it restrains the first piston to a second position in which it is disengaged from the first piston allowing the first piston to advance, the catch activated by a trigger on the exterior of the body;

the body further comprising a calibrated means for indicating the advancement of second piston and a calibrated second means for indicating the advancement of the first piston after activation by the trigger.

7. The meat probe of claim 6, wherein:

the means for advancing the piston rod comprises a second trigger hingedly attached to the interior of the body, the trigger having a passage therethrough, the piston rod passing through the passage, and co-operating plates which are biased into engagement with the second trigger, the plates selectively engaging and advancing the piston rod in an incremental fashion when the second trigger is activated.

8. The meat probe of claim 16, wherein:

the calibrated first means for indicating the advancement of the second piston comprises a longitudinal slot and calibrated markings provided adjacent and along the slot, wherein a portion of the second piston is visible through the slot.

9. The meat probe of either of claim 8 wherein said second means for indicating the advancement of the first piston is located forward of said first means for indicating the advancement of the second piston and further comprises a forward longitudinal slot and adjacent calibrated markings, wherein a portion of the second piston is visible through the forward longitudinal slot.

* * * * *